US011653825B2

(12) United States Patent
Ichihara

(10) Patent No.: US 11,653,825 B2
(45) Date of Patent: May 23, 2023

(54) IMAGING UNIT AND OBLIQUE-VIEWING ENDOSCOPE

(71) Applicant: OLYMPUS CORPORATION, Tokyo (JP)

(72) Inventor: Hirokazu Ichihara, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 252 days.

(21) Appl. No.: 17/016,489

(22) Filed: Sep. 10, 2020

(65) Prior Publication Data

US 2021/0068623 A1 Mar. 11, 2021

Related U.S. Application Data

(63) Continuation of application No. PCT/JP2019/008242, filed on Mar. 1, 2019.

(30) Foreign Application Priority Data

Mar. 14, 2018 (JP) .............................. JP2018-047049

(51) Int. Cl.
*A61B 1/05* (2006.01)
*A61B 1/00* (2006.01)
*A61B 1/06* (2006.01)

(52) U.S. Cl.
CPC .......... *A61B 1/051* (2013.01); *A61B 1/00096* (2013.01); *A61B 1/00114* (2013.01);
(Continued)

(58) Field of Classification Search
CPC ............ A61B 1/00006; A61B 1/00009; A61B 1/00071; A61B 1/00096; A61B 1/00114;
(Continued)

(56) References Cited

U.S. PATENT DOCUMENTS

2007/0118019 A1* 5/2007 Mitani ............... A61B 1/00101
600/176
2014/0264697 A1* 9/2014 Nakayama ........... H04N 5/2253
257/431

(Continued)

FOREIGN PATENT DOCUMENTS

JP H11-276424 A 10/1999
JP H11276424 A * 10/1999

(Continued)

OTHER PUBLICATIONS

International Search Report dated May 21, 2019 issued in PCT/JP2019/008242.

*Primary Examiner* — Aaron B Fairchild
*Assistant Examiner* — Julianna J Nicolaus
(74) *Attorney, Agent, or Firm* — Scully, Scott, Murphy & Presser, P.C.

(57) ABSTRACT

An imaging unit used in an oblique-viewing endoscope in which an endoscope axis along a longitudinal direction of a distal end portion of the endoscope and an optical axis of a lens unit cross along an observation direction includes: a semiconductor package including a light receiving surface arranged perpendicularly to the optical axis of the lens unit, an imaging device converting an optical image formed by the lens unit into an image signal, and a sensor electrode on a rear surface; a first circuit board including a first connecting electrode on a front surface and connected to the sensor electrode, and a second connecting electrode on a rear surface on which an electronic part is mounted; and a second circuit board including a first region including a third connecting electrode connected to the second connecting electrode, and a second region including a cable connecting electrode connected to a cable.

7 Claims, 7 Drawing Sheets

(52) U.S. Cl.
CPC ...... *A61B 1/00148* (2022.02); *A61B 1/00174* (2013.01); *A61B 1/0653* (2013.01); *A61B 1/00009* (2013.01)

(58) Field of Classification Search
CPC ............ A61B 1/00147; A61B 1/00179; A61B 1/00181; A61B 1/051; A61B 1/07; A61B 1/00174; A61B 1/00177; A61B 1/00183; A61B 1/05
USPC ........................................ 600/170, 171, 173
See application file for complete search history.

(56) References Cited

U.S. PATENT DOCUMENTS

| | | |
|---|---|---|
| 2014/0371530 A1 | 12/2014 | Wieters et al. |
| 2016/0205296 A1* | 7/2016 | Igarashi ................. H04N 5/378 348/76 |
| 2016/0249790 A1* | 9/2016 | Kitano ............... A61B 1/00117 348/65 |
| 2017/0127921 A1 | 5/2017 | Motohara et al. |
| 2018/0008133 A1* | 1/2018 | Kitano ............... A61B 1/00096 |

FOREIGN PATENT DOCUMENTS

| | | | |
|---|---|---|---|
| JP | 2001-212074 A | 8/2001 | |
| JP | 2006-239312 A | 9/2006 | |
| JP | 2015-508677 A | 3/2015 | |
| WO | WO 2016/092986 A1 | 6/2016 | |
| WO | WO-2016092986 A1 * | 6/2016 | ......... A61B 1/00114 |

* cited by examiner

IMAGING UNIT AND OBLIQUE-VIEWING ENDOSCOPE

This application is a continuation of PCT international application Ser. No. PCT/JP2019/008242 filed on Mar. 1, 2019 which designates the United States, incorporated herein by reference, and which claims the benefit of priority from Japanese Patent Applications No. 2018-047049, filed on Mar. 14, 2018, incorporated herein by reference.

BACKGROUND

The present disclosure relates to an imaging unit used in an oblique-viewing endoscope that observes an inside of a subject body from an oblique direction, and the oblique-viewing endoscope.

In the related art, an endoscope that is inserted into an inside of a subject body to enable observation of a part to be observed and various kinds of surgical treatments by using a treatment tool inserted in a treatment channel as necessary has widely been used. As this type of endoscope, in addition to a forward-viewing endoscope that observes a frontward direction, a side-viewing type and an oblique-viewing type in which an arrangement direction of a lens unit is varied are also used according to an observation direction.

As the oblique-viewing endoscope, an endoscope has been proposed in which a lens unit is arranged such that an optical axis of the lens unit is oblique to an endoscope axis, in which an imaging device is arranged parallel to the lens unit (a light receiving surface of the imaging device is arranged to be perpendicular to the optical axis of the lens unit), and in which an end portion of a flexible printed board on which electronic parts and cables are mounted and that is arranged parallel to the endoscope axis is bent to be thereby connected to a terminal of the imaging device (for example, JP-A-2006-239312).

Moreover, an oblique-viewing endoscope is proposed in which light from a lens unit arranged such that an optical axis is oblique to an endoscope axis enters a solid-state imaging device, a light receiving surface of which is arranged perpendicularly to the endoscope axis through a prism (for example, JP-A-2001-212074).

SUMMARY

An imaging unit according to one aspect of the present disclosure for being used in an oblique-viewing endoscope in which an endoscope axis extending in a longitudinal direction of a distal end portion of the oblique-viewing endoscope and an optical axis of a lens unit cross, the optical axis extending in an observation direction, includes: a semiconductor package including a light receiving surface arranged perpendicularly to the optical axis of the lens unit, art imaging device configured to convert an optical image formed by the lens unit into an image signal, and a sensor electrode formed on a rear surface of the semiconductor package; a first circuit board including a first connecting electrode provided on a front surface of the first circuit board and connected to the sensor electrode, and a second connecting electrode provided on a rear surface of the first circuit board on which an electronic part is mounted; and a second circuit board including a first region including a third connecting electrode connected to the second connecting electrode, and a second region including a cable connecting electrode to which a cable is connected.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following description, an endoscope system that includes an imaging unit will be explained as a mode (hereinafter, "embodiment") to implement the present disclosure. This embodiment is not intended to limit the present disclosure. Furthermore, in description of the drawings, like reference symbols are assigned to like parts. Moreover, the drawings are schematic illustration, and it is noted that a relation between thickness and width of respective members, a ratio among respective members, and the like differ from an actual state. Furthermore, the drawings include a part in which dimensions and ratios differ from one another thereamong.

Figure 1:
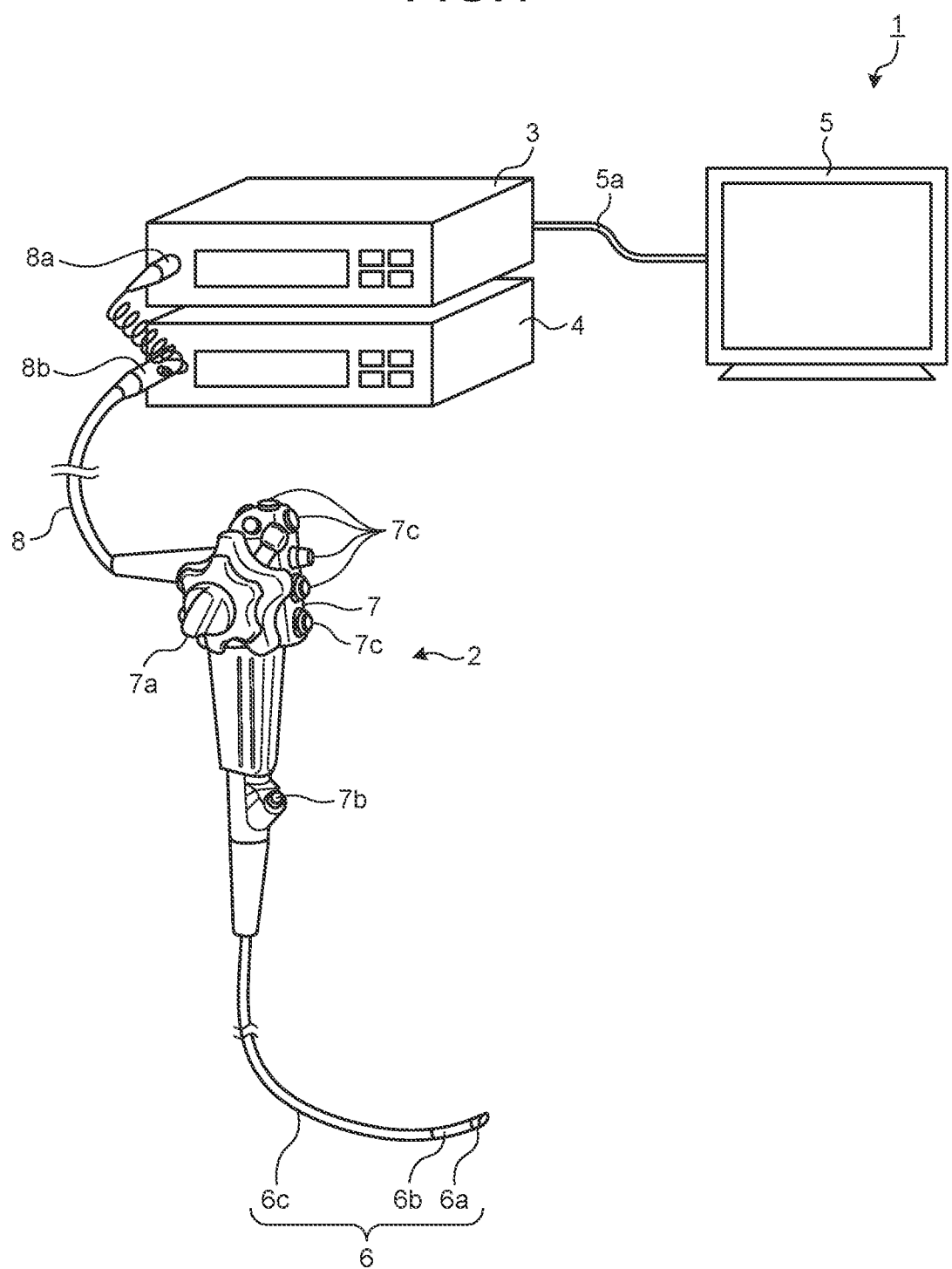
FIG. 1 is a schematic diagram illustrating an entire configuration of an endoscope system according to a first embodiment.

FIG. 1 is a schematic diagram illustrating an entire configuration of an endoscope system 1 according to a first embodiment. As illustrated in FIG. 1, the endoscope system 1 according to the first embodiment includes an endoscope 2 that is inserted into a body of a subject, and that images an inside of the body of the subject to generate an image signal of the inside, an information processing device 3 that subjects the image signal imaged by the endoscope 2 to predetermined image processing and controls respective parts of the endoscope system 1, a light source device 4 that generates illumination light of the endoscope 2, and a display device 5 that performs image display of the image signal subjected to the image processing by the information processing device 3 via a cable 5a.

The endoscope 2 is an oblique-viewing endoscope to observe the inside of the body of the subject from an oblique direction, and includes an insertion portion 6 that is inserted into the body of the subject, an operating unit 7 that is a proximal end side of the insertion portion 6, and that is held by an operator, and a flexible universal cord 8 that extends from the operating unit 7.

The insertion portion 6 is implemented by using an electric cable, an optical fiber, or the like. The insertion portion 6 includes a distal end portion 6a in which an imaging unit described later is mounted, a flexibly bendable bending portion 6b that is constituted of plural bending pieces, and flexible tube 6c that is provided on a proximal end side of the bending portion 6b, and that has flexibility. At the distal end portion 6a, a light guide cable 20 (refer to FIG. 2) to illuminate the inside of the body of the subject through an illumination lens 21 (refer to FIG. 2), an observing portion to image the inside of the body of the subject, an opening communicating with a treatment tool channel, and an air/water feed nozzle (not illustrated) are arranged.

The operating unit 7 includes a bending knob 7a to bend the bending portion 6b in an up-and-down direction and a left-and-right direction, a treatment-tool inserting portion 7b to insert a treatment tool, such as forceps and a surgical laser, into a body cavity of the subject, plural switch portions 7c to operate peripheral equipment, such as the information processing device 3, the light source device 4, an air feeding device, a water feeding device, and a gas feeding device. The treatment tool inserted from the treatment-tool inserting portion 7b is exposed from an opening at a distal end of the insertion portion 6 through the treatment channel arranged inside.

The universal cord 8 is constituted of an illumination fiber, a cable, and the like. The universal cord 8 branches at a proximal end, and one end of a branched portion is a connector 8a, and the other proximal end is a connector 8b. The connector 8a is detachable to a connector of the information processing device 3. The connector 8b is detachable to the light source device 4. The universal cord 8 propagates illumination light emitted from the light source device 4 through the connector 8b and the illumination fiber to the distal end portion 6a. Moreover, the universal cord 8 transfers an image signal imaged by an imaging unit described later to the information processing device 3 through the cable and the connector 8a.

The information processing device 3 performs predetermined information processing with respect to an image signal output from the connector 8a, and controls the entire endoscope system 1.

The light source device 4 is constituted of a light source that emits light, a condenser lens, and the like. The light source device 4 emits light from the light source under control of the information processing device 3, to provide to the endoscope 2 connected through the connector 8b and the illumination fiber of the universal cord 8 as illumination light for the inside of the body of the subject.

The display device 5 is constituted of a display using a liquid crystal or an organic electroluminescence (EL). The display device 5 displays various kinds of information including an image subjected to predetermined image processing by the information processing device 3. Thus, the operator is enabled to observe a desirable position in the body of the subject and to determine the condition by operating the endoscope 2 while viewing the image (in-vivo image) displayed by the display device 5.

Figure 2:
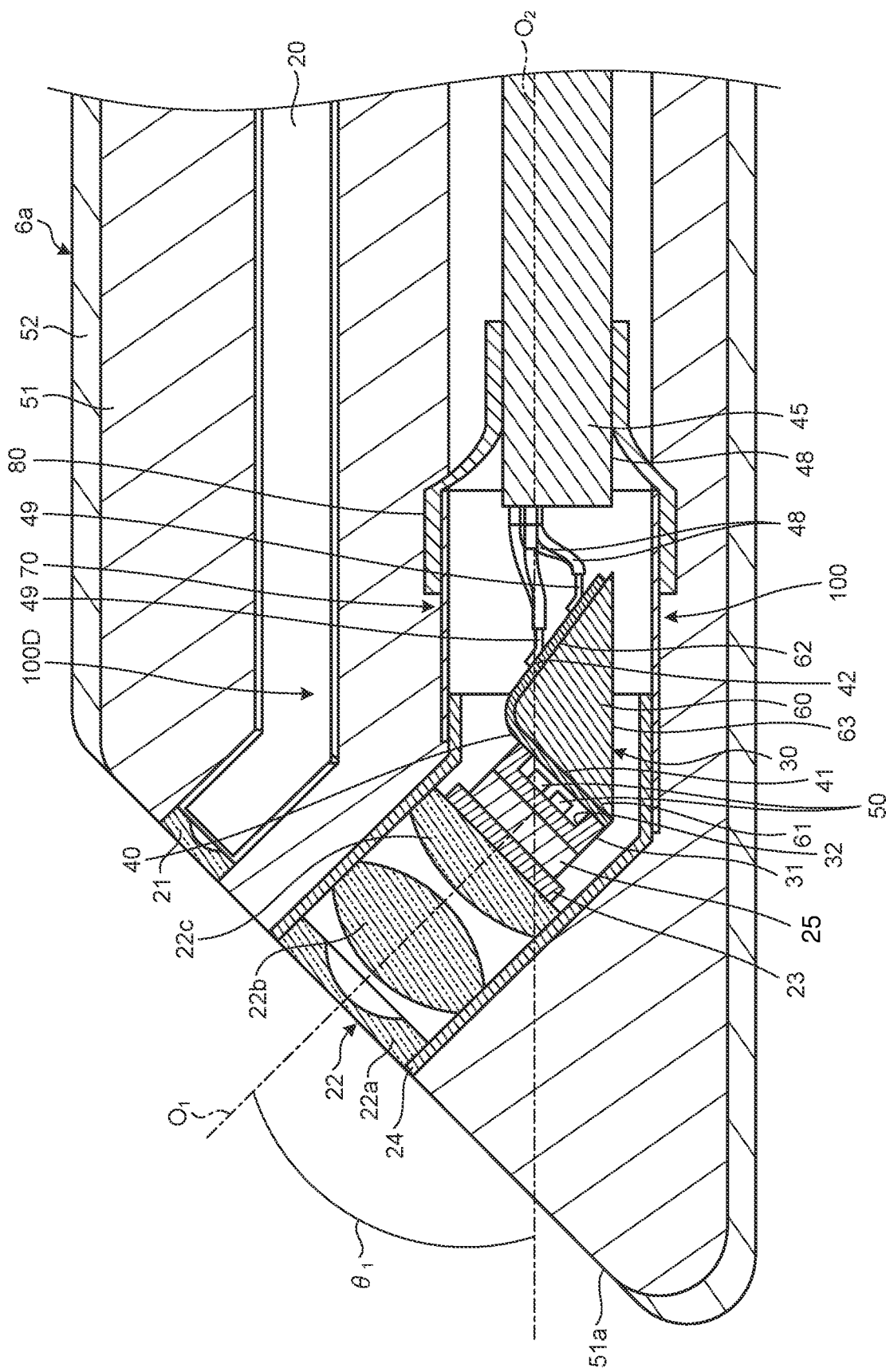
FIG. 2 is a cross-section of a distal end portion of an endoscope illustrated in FIG. 1.
Figure 3:
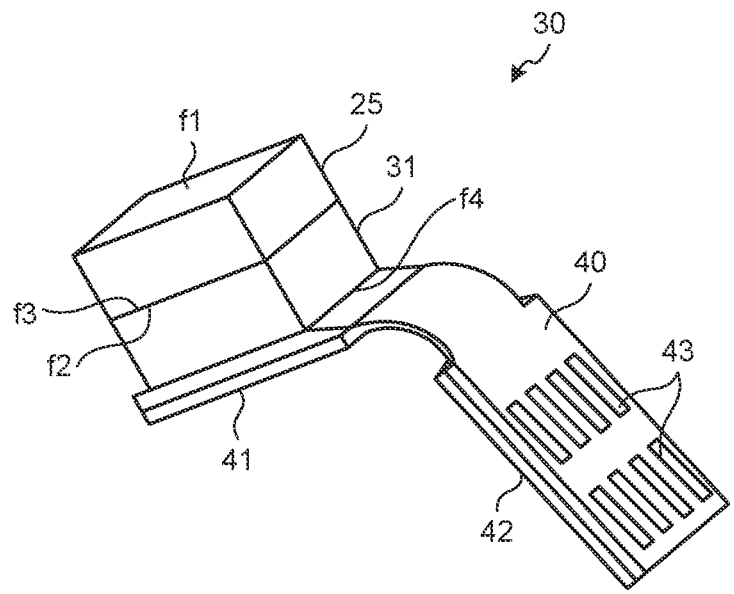
FIG. 3 is a perspective view of an imaging unit illustrated in FIG. 2.
Figure 4:
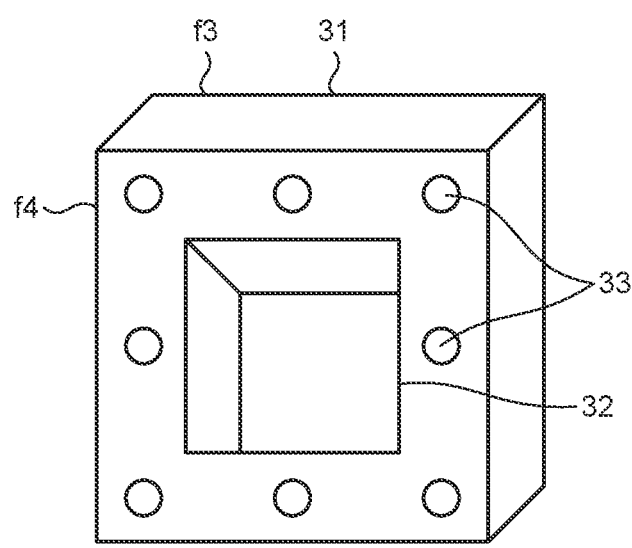
FIG. 4 is a perspective view of a first circuit board.

Next, a configuration of the distal end portion 6a of the endoscope 2 will be explained in detail. FIG. 2 is a cross-section of the distal end portion 6a of the endoscope 2. FIG. 3 is a perspective view of an imaging unit 30 illustrated in FIG. 2. FIG. 4 is a perspective view of a first circuit board 31 viewed from a rear side. FIG. 2 illustrates a cross section on a plane parallel to an optical axis $O_1$ of a lens unit 22 described later of the endoscope 2 and an endoscope axis $O_2$ (plane including the optical axis $O_1$ and the endoscope axis $O_2$). Moreover, in FIG. 3, illustration of a holding portion 60 is omitted.

An imaging device 100 includes the lens unit 22, the imaging unit 30 arranged on a proximal end side of the lens unit 22, and a bundle cable 45.

A distal-end-portion main body 51 is made of a hard member to form inner space in which an imaging device is housed. An outer periphery of the distal-end-portion main body 51 is covered with a flexible covering tube 52. A distal end surface 51a of the distal-end-portion main body 51 is formed to form an inclined surface.

The lens unit 22 includes plural objective lenses 22a, 22b, and 22c, and a lens holder 24 to hold the objective lenses 22a to 22c, and is fixed to the distal-end-portion main body 51 as this lens holder 24 interfits in the distal-end-portion main body 51 in a fixed manner. The optical axis $O_1$ of the lens unit 22 forms an angle, $\theta_1$ with the endoscope axis $O_2$, and it is arranged to intersect such that $\theta_1$ is an acute angle, that is, larger than 0° and smaller than 90°, thereby observing the inside of the body of the subject from an oblique direction.

The imaging unit 30 includes an imaging device that generates an electrical signal by subjecting an optical image received on a surface f1, which is a light receiving surface, to photoelectric conversion, and includes a rectangular-shaped semiconductor package 25 having a not illustrated sensor electrode formed on a surface f2, which is a rear surface, the first circuit board 31 that is connected to the semiconductor package 25, a second circuit board 40 that is connected to the first circuit board 31, and the holding portion that holds the second circuit board 40. The semiconductor package 25 is cemented to be fixed to the objective lens 22c through a cover glass 23.

The semiconductor package 25 is arranged such that the surface f1, which is the light receiving surface, perpendicularly intersects the optical axis $O_1$ of the lens unit 22, and light collected by the lens unit 22 enters the surface f1, which is the light receiving surface. On the surface f2 (rear surface) of the semiconductor package 25, the sensor electrode is formed. The semiconductor package 25 is preferable to be a chip size package (CSP) in which a size of an imaging device chip is to be the size of the semiconductor package 25 finally by performing wiring, electrode formation, resin sealing, and dicing on a wafer state imaging device chip.

The first circuit board 31 is a hard laminated board in which a front surface f3 and a rear surface f4 are arranged to intersect the optical axis $O_1$ of the lens unit 22 perpendicularly, and in which plural boards having a wiring formed thereon are laminated in the direction of the optical axis $O_1$. The first circuit board 31 has a rectangular shape, and has a size identical to a projection surface in a direction of the optical axis of the semiconductor package 25, or a size that fits in the projection surface. On the front surface f3 side of the first circuit board 31, a first connecting electrode connected to a sensor electrode of the semiconductor package 25 through a joint member, such as a solder ball, is formed, and on the rear surface f4 side, second connecting electrodes 33 is formed as illustrated in FIG. 4. The joint member may be a metal-core solder ball, a resin-core solder ball, an Au bump, or the like, other than the solder ball. Moreover, in a central portion on the rear surface f4 side, a concave portion 32 to mount an electronic part 50, such as a capacitor, is formed, and the second connecting electrodes 33 are formed around the concave portion. Although use of the laminated board for the first circuit board 31 facilitates formation of the concave portion 32 and arrangement of electrodes to connect an electronic part, and the like, the first circuit board 31 is not limited to the laminated board. For the laminated board, a ceramics board, a glass epoxy board, a glass board, a silicone board, and the like may be used. In terms of preventing heat generation in the semiconductor package 25, or damage of joint portions caused by differences in thermal expansion coefficient at the time of heat sterilization of the endoscope 2, the first circuit board 31 is preferable to be a ceramics board. Moreover, if a general rectangular board is used as the first circuit board 31, it may be commonized with a circuit board used in forward-viewing endoscope.

The second circuit board 40 has a first region 41 that forms an inclined surface perpendicular to the optical axis $O_1$, and a second region 42 that is arranged such that the angle θ formed with the first region 41 is an obtuse angle. In the first region 41, a not illustrated third connecting electrode to be connected to the second connecting electrode 33 is arranged, and in the second region 42, cable connecting electrodes 43 are arranged in two rows without overlapping each other in a vertical direction. The second circuit board 40 is constituted of a flexible printed board, and is bent such that the first region 41 and the second region 42 form an obtuse angle. By bending such that the first region 41 and the second region 42 form an obtuse angle, it is possible to avoid increase of diameter of the imaging unit 30, and to gain an arrangement area of the cable connecting electrodes 43. Note that the angle θ is preferable to be an obtuse angle, but is not limited to an obtuse angle. When an angle of an angle $θ_1$ between the endoscope axis $O_2$, which is in a longitudinal direction of the distal end portion 6a of the endoscope and the optical axis $O_1$ of the lens unit, which is the observing direction, is small, even if the angle θ is an acute angle, it is possible to avoid increase of diameter, and to gain a wiring area.

The holding portion 60 has a fourth region 61 that abuts on the first region 41, a fifth region 62 that abuts on the second region 42, and a sixth region 63 that forms an acute angle with the fourth region 61 and the fifth region 62, respectively, and that is arranged in parallel with the endoscope axis $O_2$. The holding portion 60 holds the first region 41 and the second region 42 of the second circuit board 40 by abutting thereon, in the fourth region 61 and the fifth region 62. By holding the second circuit. board 40 with the holding portion 60, an angle formed between eh first region 41 and the second region may be maintained at a predetermined angle. Moreover, by pushing the second circuit board 40 with the holding portion 60, it may be bent such that the first region 41 and the second region 42 form a predetermined angle. By holding the second circuit board 40 with the holding portion 60, the second circuit board 40 is fixed by the holding portion 60 at the time when the first circuit board 31 and the second circuit board 40 are connected, and when a signal cable 48 is connected to the second circuit board 40 also and, therefore, the connecting work is facilitated.

The lens holder 24 that holds the lens unit 22 functions as a holding frame that surrounds the semiconductor package 25, the first circuit board 31, the second circuit board 40, and the holding portion 60. In the first embodiment, one piece of the lens holder 24 holds the lens unit 22 and surrounds the first circuit board 31, the second circuit board 40, and the holding portion 60, but it may be structured such that, in addition to the lens holder 24, an imaging frame that holds the semiconductor package 25 through the cover glass 23, a shield frame, and the like surround the first circuit board 31, the second circuit board 40, and the holding portion 60. In such a case, the lens holder, the imaging frame, and the shield frame function as the holding frame.

Figure 5:
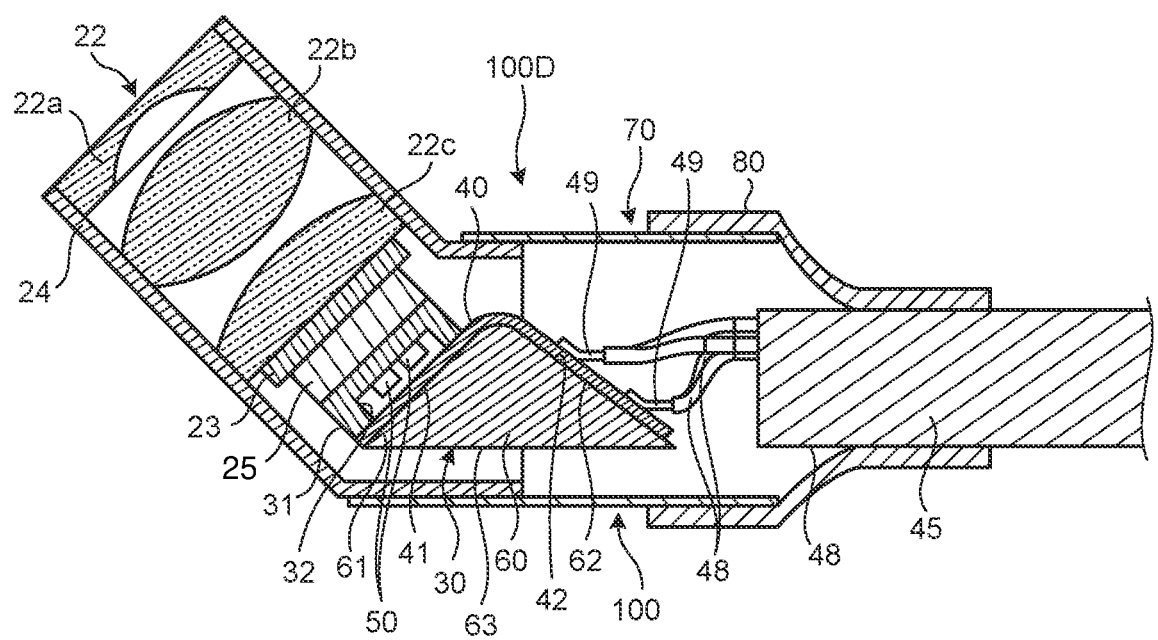
FIG. 5 is a cross-section of an imaging device according to a first modification of the first embodiment.
Figure 6:
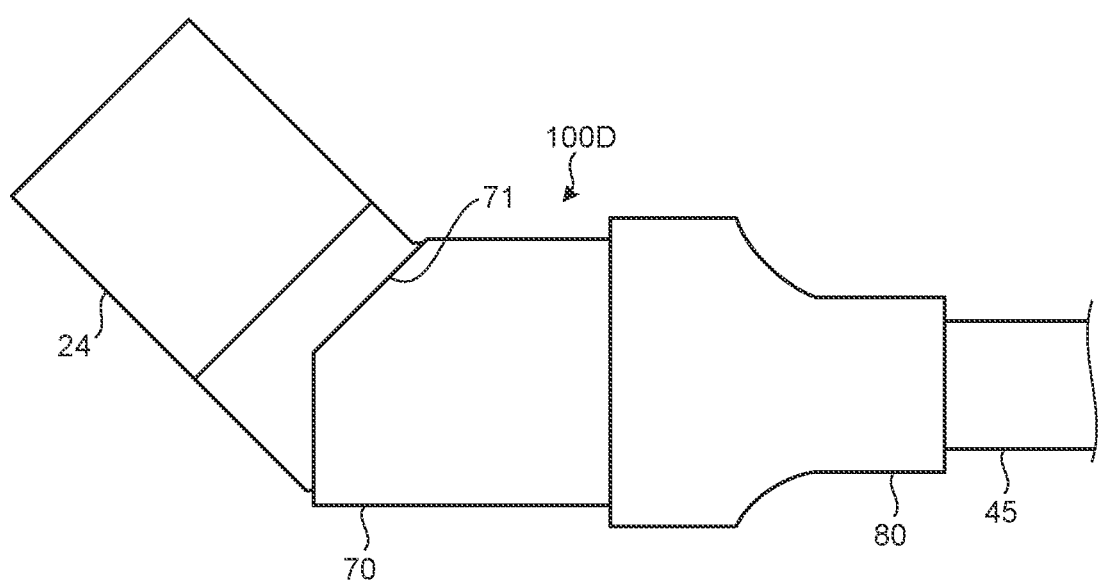
FIG. 6 is a side view of the imaging device illustrated in FIG. 5.

FIG. 5 is a cross-section of an imaging device 100D according to a first modification of the first embodiment. FIG. 6 is a side view of the imaging device 100D illustrated in FIG. 5. The imaging device 100D includes the lens unit 22, the imaging unit 30 arranged on the proximal end side of the lens unit 22, the bundle cable 45, a shield frame 70, and a heat shrinkable tube 80.

The shield frame 70 has a substantially rectangular prism having a hollow inside, and a distal end portion interfits in an outer periphery of the lens holder 24 on a proximal end side. In a distal end portion of the shield frame 70, a notch 71 to avoid interference with a portion parallel to the optical axis $O_1$ of the lens holder 24 is arranged. A proximal end portion of the shield frame 70 and a distal end portion of the bundle cable 45 are covered with the heat shrinkable tube 80. With the above structure, the dependability of the joint portion of the imaging device 100D may be improved.

The bundle cable 45 that bundles the signal cables 48 is inserted in the insertion portion 6, and is extended to the connectors 8a and 8b through the operating unit 7 and the universal cord 8 illustrated in FIG. 1. A cable core 49 of the signal cable 48 is connected to the cable connecting electrode 43 of the second circuit board 40 by a connecting member, such as solder.

An optical image formed by the objective lenses 22a to 22c of the lens unit 22 is converted into an image signal by an imaging device arranged at an image forming position of the objective lenses 22a to 22c, and is transmitted to the information processing device 3 through the first circuit board 31, the second circuit board 40, and the signal cable 48.

According to the imaging unit 30 of the first embodiment, the semiconductor package 25 and the first circuit board 31 are arranged such that the light receiving surface f1 and the front surface f3 are perpendicular to the optical axis $O_1$, and the first circuit board 31 in which an electronic part is mounted on the rear surface f4 is connected to the rear surface f2 of the semiconductor package 25. Because the electronic part 50 may be arranged near the semiconductor package 25, increase of an impedance may be suppressed, and noises may be reduced. Moreover, by applying a board of a material having a linear expansion coefficient close to that of the semiconductor package 25 as the first circuit board 31, for example, a ceramics board, the connection dependability when a heat load is applied may be improved.

In the first embodiment, the circuit board is divided into the first circuit board 31 on which the electronic part 50 is mounted, and the second circuit board 40 to which the signal cable 48 is connected. By dividing the circuit board in to the first circuit board 31 and the second circuit board 40, a heat load on the semiconductor package 25 when the second circuit board 40 is connected to the first circuit board 31, and when the signal cable 48 is connected to the cable connecting electrode 43 may be reduced, and deficiencies, such as disconnection of the joint portion, may be reduced.

The holding portion 60 used in the first embodiment has a triangular prism, but it is only necessary to be able to hold the second circuit board 40, and it may be a triangular prism having a hollow inside. Moreover, a structure in which a metallic plate is bent, that is, a structure that is constituted only of the fourth region 61 and the fifth region 62 without the sixth region 63 may be applied. Furthermore, the cable connecting electrode 43 may be formed in the holding portion 60, to connect the signal cable 48. Moreover, the holding portion 60 may be used only at the time of manufacture of the imaging unit 30, for example, at the time of connecting the signal cable 48 to the second circuit board 40, or at time of connecting the first circuit board 31 and the second circuit board 40, and may be removed from an end product.

Figure 7:
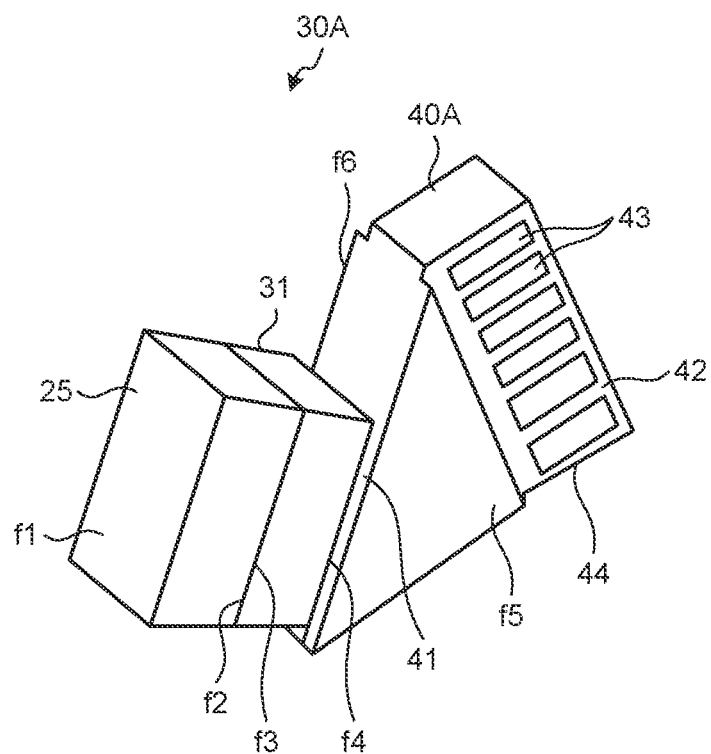
FIG. 7 is a perspective view of an imaging unit according to a second modification of the first embodiment.

In the first embodiment described above, a flexible printed board is used as the second circuit board 40, but a ceramics board or a molded interconnect device (MID) board may be used also. FIG. 7 is a perspective view of an imaging unit 30A according to a second modification of the first embodiment.

In the imaging unit 30A, the semiconductor package 25 and the first circuit board 31 have configurations similar to those of the first embodiment.

The second circuit board 40A is a ceramics laminated board that includes the first region 41 forming an inclined surface perpendicular to the optical axis $O_1$ and the second region 42 in which the cable connecting electrode 43 is arranged on a side surface f5 and a side surface f6. The board is laminated in parallel to the side surface f5 and the side surface f6. A stepped portion 44 is formed at a proximal end portion of the second circuit board 40A, and the cable connecting electrode 43 is formed at the stepped portion 44.

In the imaging unit 30A according to the first modification of the present embodiment, similarly to the first embodiment, the electronic part 50 may be arranged near the semiconductor package 25 and, therefore, increase of impedance may be suppressed, and noises may be reduced. Moreover, by dividing the circuit board into the first circuit board 31 in which the electronic part 50 is mounted and the second circuit board 40A to which the signal cable 48 is connected, a heat load on the semiconductor package 25 when the second circuit board 40A is connected to the first circuit board, and when the signal cable 48 is connected to the cable connecting electrode 43 may be decreased, and deficiencies, such as disconnection of the joint portion, may be reduced. Furthermore, because the second circuit board 40A is a ceramics board, which is a hard board, the connecting work is facilitated without using the holding portion 60.

Figure 8:
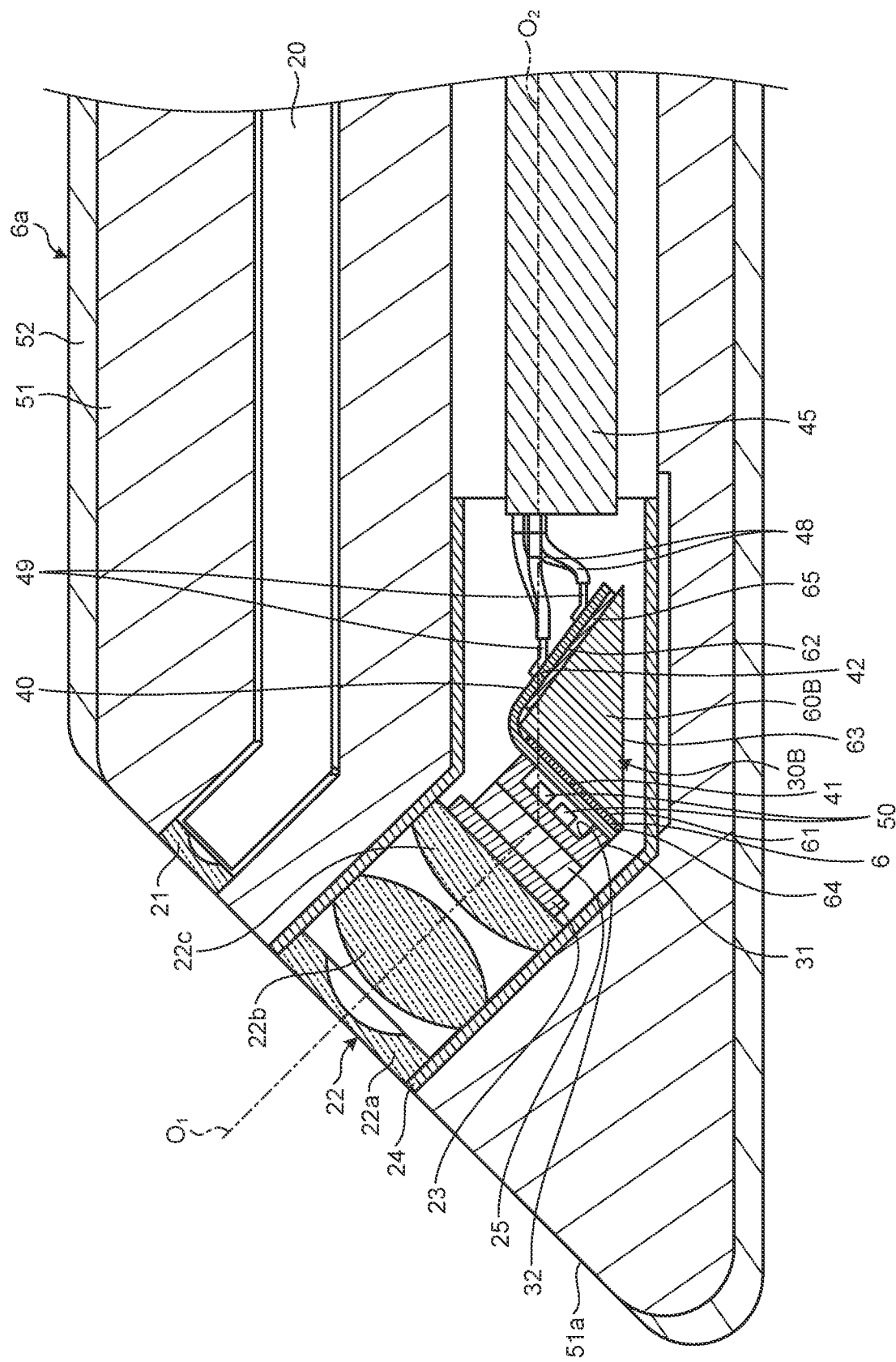
FIG. 8 is a cross-section of a distal end portion of an endoscope according to a second embodiment.

FIG. 8 is a cross-section of the distal end portion 6a of an endoscope according to a second embodiment. In an imaging unit 30B according to the second embodiment, the second circuit board 40 and a holding portion 60B are connected with a first joint portion 64 and a second joint portion 65.

In the imaging unit 30B according to the second embodiment, the semiconductor package 25, the first circuit board 31, and the second circuit board 40 have configurations similar to those of the first embodiment.

The first joint portion 64 connects the first region 41 and the fourth region 61. The second joint portion 65 connects the second region 42 and the fifth region 62. The first joint portion 64 is constituted of a material having a thermal conductivity higher than the second joint portion 65.

The holding portion 60B is made from a highly thermal conductive material. Because the imaging device of the semiconductor package 25 generates heat when the imaging unit 30B is activated, it is necessary to dissipate heat efficiently. The heat transmitted from the semiconductor package 25 to the first circuit board 31 is transmitted to a holding portion made from a highly thermal conductive material through the second circuit board 40 and the first joint portion 64, and the heat may be efficiently dissipated.

On the other hand, it is heated when the signal cable 48 is connected to the cable connecting electrode 43 of the second circuit board 40, because dissipation of the applied heat from the holding portion 60B through the second joint portion 65 is suppressed, by using a material having low thermal conductivity for the second joint portion 65, degradation of the energy efficiency may be suppressed.

As for an imaging unit efficient in heat dissipation, in addition to the imaging unit 30B of the second embodiment, for example, by applying a MID or a ceramics board used in the first modification of the first embodiment to the second circuit board, and by arranging a ground plane on a surface region other a region used for the first region and the second region, heat may be dissipated through this ground plane also.

In the present disclosure, an electronic part, such as a capacitor, is mounted on a first circuit board connected to a rear surface of a semiconductor package, and is connected to the first circuit board through a first region forming an inclined surface that is perpendicular to an optical axis of a second circuit board, and it is thereby possible to prevent degradation of image quality by preventing occurrence of noises. Because a prism is not used, an imaging unit and an oblique-viewing endoscope that are low-cost and easy to perform assembly adjustment may be obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An imaging unit for being used in an oblique-viewing endoscope in which an endoscope axis extending in a longitudinal direction of a distal end portion of the oblique-viewing endoscope and an optical axis of a lens unit cross, the optical axis extending in an observation direction, the imaging unit comprising:
    a semiconductor package including a light receiving surface arranged perpendicularly to the optical axis of the lens unit, the semiconductor package including an image sensor configured to convert an optical image formed by the lens unit into an image signal;
    a first circuit board on which an electronic part is mounted, the first circuit board including a front surface and a rear surface, the front surface of the first circuit board being connected to a rear surface of the semiconductor package, the rear surface of the first circuit board being provided with a second connecting electrode;
    a second circuit board including
        a first region including a third connecting electrode connected to the second connecting electrode, and
        a second region including a cable connecting electrode to which a cable is connected;
    a holding frame configured to hold the lens unit; and
    a holding portion configured to hold the second circuit board, wherein the second circuit board is a flexible printed board, and the second region is bent such that an angle θ formed with the first region is an obtuse angle, and
    the holding portion includes
        a fourth region configured to abut on the first region,
        a fifth region configured to abut on the second region, and
        a sixth region configured to respectively intersect the fourth region and the fifth region at an acute angle, the sixth region being parallel to the endoscope axis.

2. The imaging unit according to claim 1, wherein
    the first circuit board includes a concave portion in a central portion of the rear surface of the first circuit board,
    the electronic part is mounted in the concave portion, and
    the second connecting electrode is arranged around the concave portion.

3. The imaging unit according to claim 1, wherein
    the holding portion is made of a highly heat conductive material, and the first region and the fourth region are bonded with a material having a heat conductivity higher than that of a material bonding the second region and the fifth region.

4. The imaging unit according to claim 1, wherein the holding portion includes a cable connecting electrode to which a cable is connected, the cable connecting electrode being arranged on a front surface of the holding portion.

5. An oblique-viewing endoscope comprising:
the imaging unit according to claim 1; and
an insertion portion in which the imaging unit is arranged at a distal end of the insertion portion.

6. An imaging unit for being used in an oblique-viewing endoscope in which an endoscope axis extending in a longitudinal direction of a distal end portion of the oblique-viewing endoscope and an optical axis of a lens unit cross, the optical axis extending in an observation direction, the imaging unit comprising:
a semiconductor package including a light receiving surface arranged perpendicularly to the optical axis of the lens unit, the semiconductor package including an image sensor configured to convert an optical image formed by the lens unit into an image signal;
a first circuit board on which an electronic part is mounted, the first circuit board including a front surface and a rear surface, the front surface of the first circuit board being connected to a rear surface of the semiconductor package, the rear surface of the first circuit board being provided with a second connecting electrode; and
a second circuit board including
a first region including a third connecting electrode connected to the second connecting electrode, and
a second region including a cable connecting electrode to which a cable is connected, wherein
the second circuit board is a flexible printed board, and the second region is bent such that an angle θ formed with the first region is an obtuse angle.

7. An oblique-viewing endoscope comprising:
the imaging unit according to claim 6; and
an insertion portion in which the imaging unit is arranged at a distal end of the insertion portion.

* * * * *